United States Patent
Alfieri et al.

(10) Patent No.: US 6,726,717 B2
(45) Date of Patent: Apr. 27, 2004

(54) ANNULAR PROSTHESIS FOR MITRAL VALVE

(75) Inventors: Ottavio Alfieri, Brescia (IT); Francesco Maisano, Milan (IT); Alberto Redaelli, Milan (IT)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 10/144,932

(22) Filed: May 15, 2002

(65) Prior Publication Data

US 2002/0173844 A1 Nov. 21, 2002

(30) Foreign Application Priority Data

May 17, 2001 (IT) ...................... MI2001A1012

(51) Int. Cl.[7] .................................. A61F 2/24
(52) U.S. Cl. ...................... 623/2.36; 623/2.38; 623/2.37
(58) Field of Search ............. 623/2.36, 2.37, 623/2.38, 2.39

(56) References Cited

U.S. PATENT DOCUMENTS

| | | | |
|---|---|---|---|
| 4,055,861 A | * | 11/1977 | Carpentier et al. ........ 623/2.36 |
| 5,607,471 A | * | 3/1997 | Seguin et al. ............... 623/2.36 |
| 6,019,739 A | | 2/2000 | Rhee et al. |
| 6,102,945 A | | 8/2000 | Campbell |
| 6,217,610 B1 | * | 4/2001 | Carpentier et al. ........ 623/2.37 |

OTHER PUBLICATIONS

Edwards Lifesciences. Carpentier–Edwards Classic Mitral Annuloplasty Ring. Feb. 12, 2001. www.ctsnet.org/edwards/products/702.*

* cited by examiner

Primary Examiner—David H. Willse
Assistant Examiner—Kamrin Landrem
(74) Attorney, Agent, or Firm—John Christopher James

(57) ABSTRACT

The present invention refers to an annular prosthesis for mitral valve. In one of its embodiments the annular prosthesis for mitral valve is made up of a posterior half-ring and an anterior half-ring coupled to each other on a first transverse plane which defines a maximum width section of the prosthesis, characterised in that the ratio between the distance between said anterior half-ring and said posterior half-ring, as measured along a second plane, perpendicular to said first plane and equidistant to said couplings, and said maximum width of the prosthesis is lower than 3/4.

14 Claims, 1 Drawing Sheet

ANNULAR PROSTHESIS FOR MITRAL VALVE

The present invention refers to an annular prosthesis for mitral valve.

The mitral plastic surgery operation includes a series of procedures suitable to re-establish the correct functionality of the mitral valve, when this is affected by congenital or acquired pathology. Among these procedures, the remodelling of the valve annulus is one of the most frequently used manoeuvres in order to complete and/or to strengthen the valve. Remodelling provides for two moments: the reduction of the annular area and the properly said remodelling, that is suitable to re-establish the normal geometric ratios that are found in natural valves free of pathology. The first one of these manoeuvres is usually carried out with the aid of a prosthesis that is appropriately sutured to the natural annulus. The prosthesis for anuloplastic surgery available on the market are of two types. Flexible annular prostheses, made of various materials, that allow a "linear" reduction of the annular circumference, and rigid and semi-rigid annular prostheses made of various materials, that allow the "linear" reduction of the annular circumference and a geometric remodelling so as to re-establish the physiological systolic shape of the annulus. In the case of semi-rigid prostheses they additionally allow a minimum deformation in order to allow the prosthesis to follow the deformations of the annulus during the cardiac stages.

All the rigid and semi-rigid annular prostheses have a kidney-like or coupled D shape, with an anterior half-ring, rectilinear in first approximation, that gets sutured in correspondence of the joining of the anterior valve leaflet and a curved posterior half-ring that is sutured in correspondence of the joining of the posterior valve leaflet. The shape of the annular prostheses at issue reproduces the configuration of the valve annulus during the ventricular systole, and therefore in the stage of the valve closing. The ratio between minor axis and major axis is approximately 3/4 in all the models currently on the market since it reproduces normal anatomical ratios.

Recently the concept of undersizing of mitral valve anuloplasty has been introduced. This procedure is proposed in case of mitral insufficiency due to a reduced movement of the leaflets as in the case of ischaemic mitral valve or dilated cardiomyopathy. The undersizing consists in using a ring smaller than necessary, though still maintaining the ratio of approximately 3/4, and it is carried out in order to bring the base of the anterior leaflet even closer to the posterior leaflet in order to increase the coaptation surface (closure).

The Applicants noticed that in certain pathological conditions, there is a need to modify such ratio in order to make the operation of reconstruction of the mitral valve more effective: for instance in order to bring the valve leaflets closer to each other in the case of anatomical or functional tissue deficiency of one or both leaflets. In addition, it has also been observed that anatomical variation that do not correspond to the ratios reported above are frequent in nature.

In view of the state of the art herein described, a scope of the present invention is to provide an annular prosthesis for mitral valve that can meet the different requirements that have been noticed.

According to present the invention, these and other scopes have been attained by means of an annular prosthesis for mitral valve made up of a posterior half-ring and an anterior half-ring that are coupled to each other on a first transverse plane which defines a maximum width section of the prosthesis, characterised in that the ratio between the distance between said anterior half-ring and said posterior half-ring, as measured along a second plane, perpendicular to said first plane and equidistant to said couplings, and said maximum width of the prosthesis is lower than 3/4.

The characteristics and the advantages of the present invention will become evident from the following detailed description of an embodiment thereof, that is illustrated as a non-limiting example in the enclosed drawings, in which.

Figure 1:
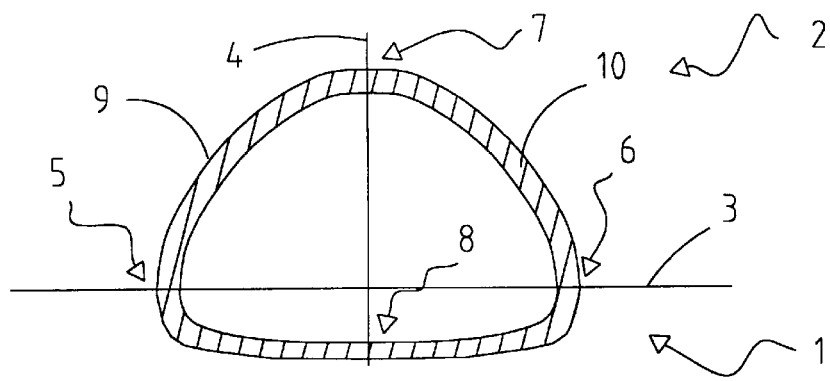
FIG. 1 shows an annular prosthesis for mitral valve according to the known art.

In FIG. 1 a prosthesis for annular mitral valve according to the known art is shown. It has a kidney-like or D-shape, and it is made up of an anterior half-ring 1 rectilinear in first approximation, that is sutured in correspondence of the joining of the anterior valve leaflet 2 and a curved posterior half-ring that is sutured in correspondence of the joining of the posterior valve leaflet. The posterior half-ring 2 and anterior half-ring 1 are coupled at two points 5 and 6 located on a transverse plane 3 that define a maximum width section of the prosthesis. In addition a longitudinal plane 4 is also defined, that intersects the prosthesis at the points 7 and 8, that is arranged perpendicular to the transverse plane 3 and equidistant from the coupling points 5 and 6. The posterior half-ring 2 is thus subdivided in a first lateral zone (left) 9 located between the points 5 and 7, and a second lateral zone (right) 10 located between the points 6 and 7. The intersection points 5, 6 and 7, 8 of the prosthesis respectively with the planes 3 and 4 define the terms for the calculation of the dimensions of the prosthesis. According to the known art, the ratio between the distance between the points 7 and 8, herein also defined as height of the prosthesis, and the distance between the points 5 and 6, herein also defined as width of the prosthesis, is typically equal to 3/4.

Figure 2:
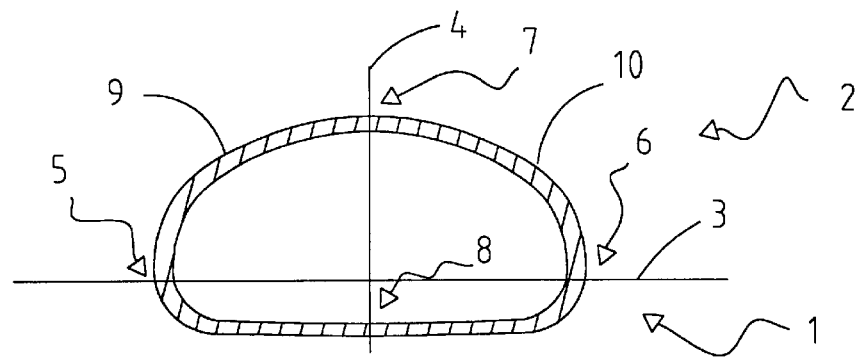
FIG. 2 shows a first embodiment of an annular prosthesis for mitral valve according to the present invention.

In FIG. 2 a first embodiment of an annular prosthesis for mitral valve according to the present invention is shown. It substantially has the same shape as the one rendered in FIG. 1 but the ratio between the height and the width of the prosthesis is lower than 3/4, for instance equal to 2.5/4 or equal to 2/4.

For every size of prosthesis two or more reduced ratios can therefore be provided. By size the dimension of the transverse width of the prosthesis is meant; it represents the clinical parameter on the bases of which the prosthesis is selected in each single clinical case in examination, and it is also the identifying parameter for the prosthesis.

The lower ratio as compared with the prostheses currently used for annuloplastic surgery allows its use in selected cases of pathologies that are not treatable in adequate way with conventional prostheses.

The lower ratios in this case have the function to treat pathologies characterised by reduced movement of the leaflets with tethering (stretching towards the cardiac apex) symmetrical (as regards each leaflet) with medium or serious proportions. The reduction of the ratio confers the prosthesis a more "squeezed" shape, that allows a better apposition of the leaflets in selected cases. For instance, in the dilated cardiomyopathy, when the expansion of the left ventricle determines a lateral movement and toward the apex of the papillary muscles, the leaflets stretch toward the cardiac apex and the apposition is thus lacking at central level. A possible sizing, in addition, must respect an anatomical requirement: the anterior half-ring 1 (the base for the implant of the front leaflet) is anatomically fixed and not modifiable, and therefore, the sizing should not be applied to this structure, that is to the width of the prosthesis. The maintaining of a normal fore width of the prosthesis, associated with the reduction of the height allows an undersizing that is less inclined to deformation of the fore leaflet, therefore reducing the risk of residual insufficiency.

Figure 3:
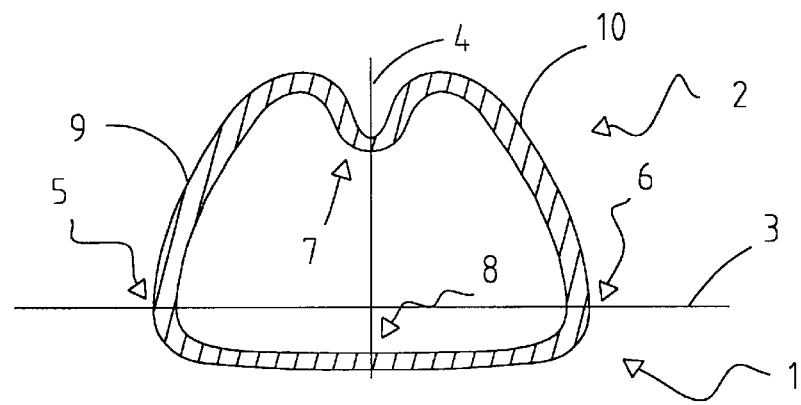
FIG. 3 shows a second embodiment of an annular prosthesis for mitral valve according to the present invention.

In FIG. 3 a second embodiment of an annular prosthesis for mitral valve according to the present invention is shown. In this case the natural ratio height/width of 3/4 is maintained in order to define the curving radii of the two lateral parts of the anterior half-ring. In the central zone, in proximity of the point 7, the distance between the posterior half-ring 1 and the front half-ring 2 is reduced, with the aim of obtaining a height/width ratio lower than 3/4. The central zone of the posterior half-ring 2 therefore takes a configuration that recalls the dog bone or gull wing shape and increases the coaptation at central level by limiting the annular reduction at level of the commisure.

In some extreme cases, it could be useful to make the distance between the two half-rings in the central zone equal to zero, in order to obtain an eight-shape configuration, in order to improve the coaptation at central level. This remodelling simulates the double orifice operation, in which the leaflets are joined at the centre of the valve in order to force the central coaptation. This prosthesis could also be used with this type of technique in order to reduce the stress on the suture and in order to minimise the reduction of the valve area.

Figure 4:
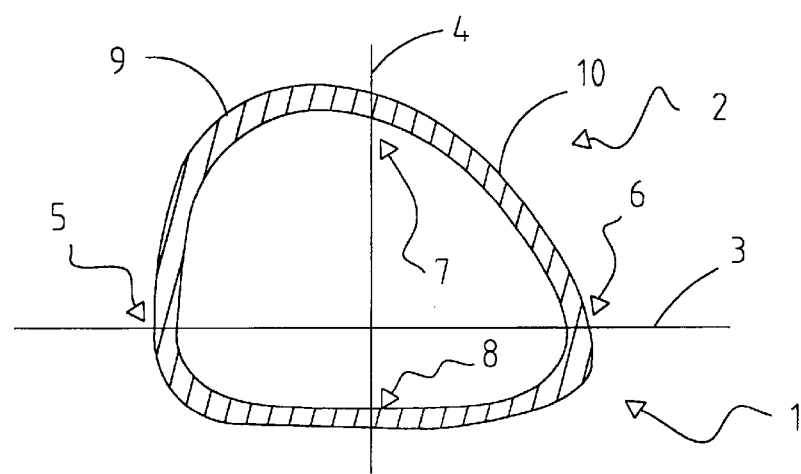
FIG. 4 shows a third embodiment of an annular prosthesis for mitral valve according to the present invention.

In FIG. 4 a third embodiment of an annular prosthesis for mitral valve according to the present invention is shown.

In this embodiment the curving radius of one of the lateral zones, for instance the second lateral zone (right) 10, is increased so as to induce a selective increase of the competence in correspondence of the valve sector with reduced mobility of the leaflets (bad asymmetric apposition of the leaflets as in ischaemic pathology). It is thus obtained that one part of the prosthesis, for instance the first lateral zone (left) 9, maintains a configuration substantially similar to the traditional prosthesis and one part, for instance the second lateral zone (right) 10, gets a sized configuration. In other words the distance between the middle point of the first lateral zone (left) 9 and the longitudinal plane 4 is greater than the distance between the middle point of the second lateral zone (right) 10 and the longitudinal plane 4.

The prosthesis, according to the present invention, can be made of an inert material that is highly tolerated by the human organism and can have a resistance that is appropriated to the use and that can substantially maintain the shape given to it.

What is claimed is:

1. An annular prosthesis for a mitral valve comprising a posterior half-ring and an anterior half-ring coupled to each other on a first transverse plane at two coupling points, the first transverse plane defining a maximum width section of the prosthesis, wherein the ratio between (a) the distance between said anterior half-ring and said posterior half-ring, as measured along a second plane that is perpendicular to the first plane and equidistant to said coupling points and (b) the maximum width of said prosthesis is lower than 3/4.

2. The annular prosthesis of claim 1, wherein said ratio is lower than or equal to 2.5/4.

3. The annular prosthesis of claim 1, wherein said posterior half-ring has a gull wing shape.

4. The annular prosthesis of claim 3, wherein said posterior half-ring is symmetrical with respect to the second plane.

5. The annular prosthesis of claim 1, wherein said posterior half-ring is symmetrical with respect to the second plane.

6. The annular prosthesis of claim 1, wherein is said posterior half-ring is asymmetrical with respect to the second plane.

7. The annular prosthesis of claim 6, wherein one lateral portion of said posterior half-ring has a radius of curvature that is smaller than the other lateral portion of said posterior half-ring.

8. An annuloplasty ring for a mitral valve comprising a posterior half-ring and an anterior half-ring coupled to each other on a first transverse plane at two coupling points, the first transverse plane defining a maximum width section of the ring, wherein the ratio between (a) the distance between said anterior half-ring and said posterior half-ring, as measured along a second plane that is perpendicular to the first plane and equidistant to said coupling points, and (b) the maximum width of said ring is lower than 3/4.

9. The annuloplasty ring of claim 8, wherein said ratio is lower than or equal to 2.5/4.

10. The annuloplasty ring of claim 8, wherein said posterior half-ring has a gull wing shape.

11. The annuloplasty ring of claim 10, wherein said posterior half-ring is symmetrical with respect to the second plane.

12. The annuloplasty ring of claim 8, wherein said posterior half-ring is symmetrical with respect to the second plane.

13. The annuloplasty ring of claim 8, wherein is said posterior half-ring is asymmetrical with respect to the second plane.

14. The annuloplasty ring of claim 13, wherein one lateral portion of said posterior half-ring has a radius of curvature that is smaller than the other lateral portion of said posterior half-ring.

\* \* \* \* \*